United States Patent [19]
Falk

[11] Patent Number: 5,948,350
[45] Date of Patent: Sep. 7, 1999

[54] DEVICE FOR DISPENSING ADDITIVE IN MOLTEN METAL SAMPLE MOLD

[75] Inventor: Richard A Falk, Hillsboro Beach, Fla.

[73] Assignee: Midwest Instrument Co., Inc., Hartland, Wis.

[21] Appl. No.: 09/022,063

[22] Filed: Feb. 11, 1998

[51] Int. Cl.[6] .................................................. G01N 1/12
[52] U.S. Cl. ............................ 266/80; 266/78; 73/864.54
[58] Field of Search .................... 266/78, 80; 73/DIG. 9, 73/864.58

[56] References Cited

U.S. PATENT DOCUMENTS

| | | |
|---|---|---|
| 3,295,171 | 1/1967 | Strange et al. . |
| 3,452,602 | 7/1969 | Hackett . |
| 3,546,921 | 12/1970 | Bourke et al. . |
| 3,818,762 | 6/1974 | Kraus et al. . |
| 4,107,393 | 8/1978 | Frantzreb, Sr. et al. . |
| 4,140,019 | 2/1979 | Falk . |
| 4,261,740 | 4/1981 | Plessers . |
| 4,274,284 | 6/1981 | Hance . |
| 4,326,426 | 4/1982 | Falk . |
| 4,396,792 | 8/1983 | Falk . |
| 4,503,716 | 3/1985 | Wuensch . |
| 4,535,640 | 8/1985 | Falk . |
| 5,057,149 | 10/1991 | Conti et al. . |
| 5,524,497 | 6/1996 | Falk . |

Primary Examiner—Scott Kastler
Attorney, Agent, or Firm—Ryan Kromholz & Manion

[57] ABSTRACT

A mold for sampling molten metals includes a cavity body for receiving a measured sample of a molten metal, and, an insert containing a material for promoting carbide formation in the molten metal as it cools, the insert containing a measured amount of the material in finely divided solid form. The insert may be adhered to a recess in the mold surface or within a fill inlet passage and is preferably in the form of an enclosed tube formed of thin-walled material which contains the carbide formation promoting material in finely divided solid form. The insert may be formed of a metal closed at one end by a plastic adhesive material which opens upon immersion to release a stream of the carbide formation promoting material into the fill opening of the mold.

10 Claims, 4 Drawing Sheets

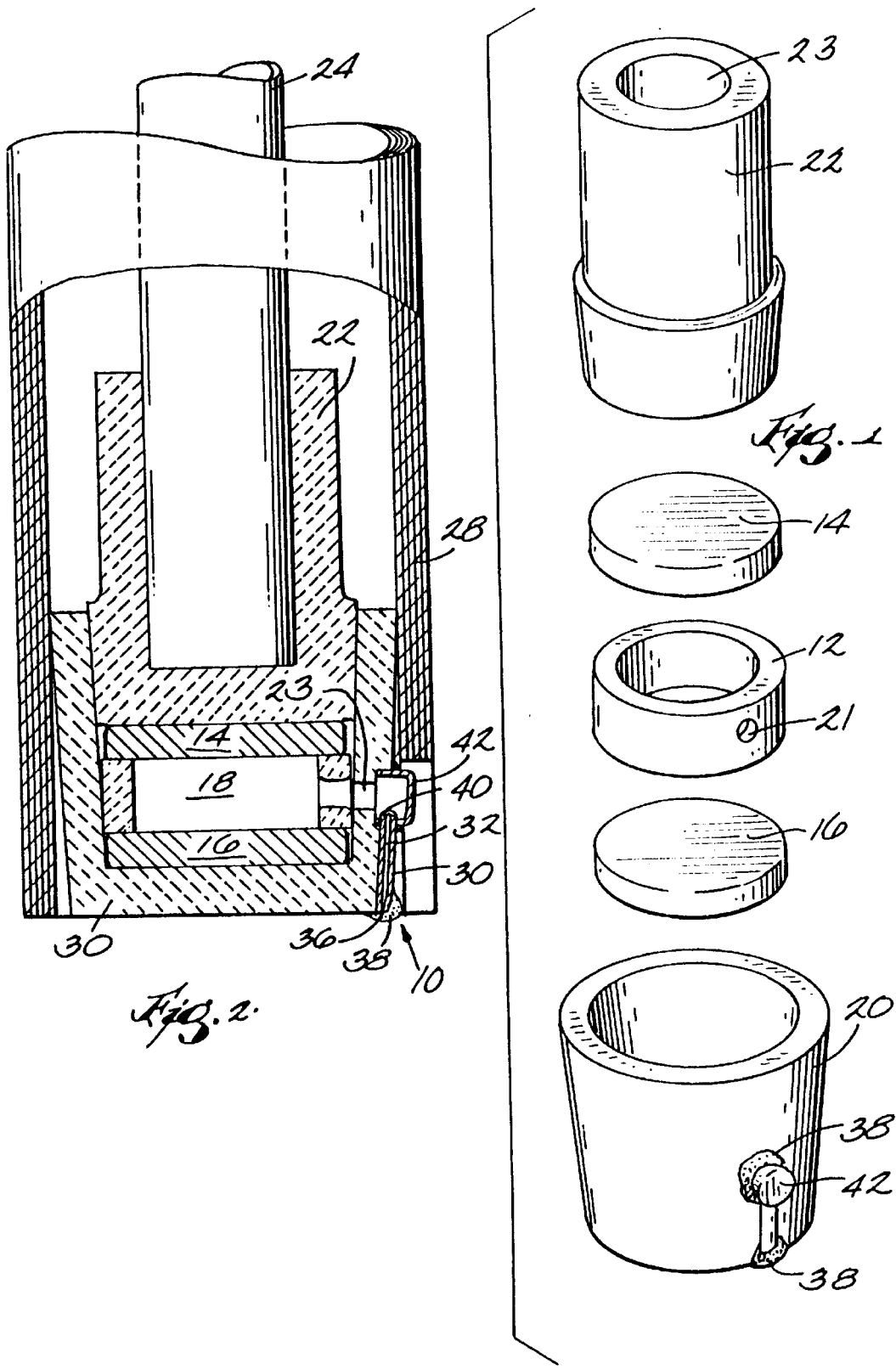

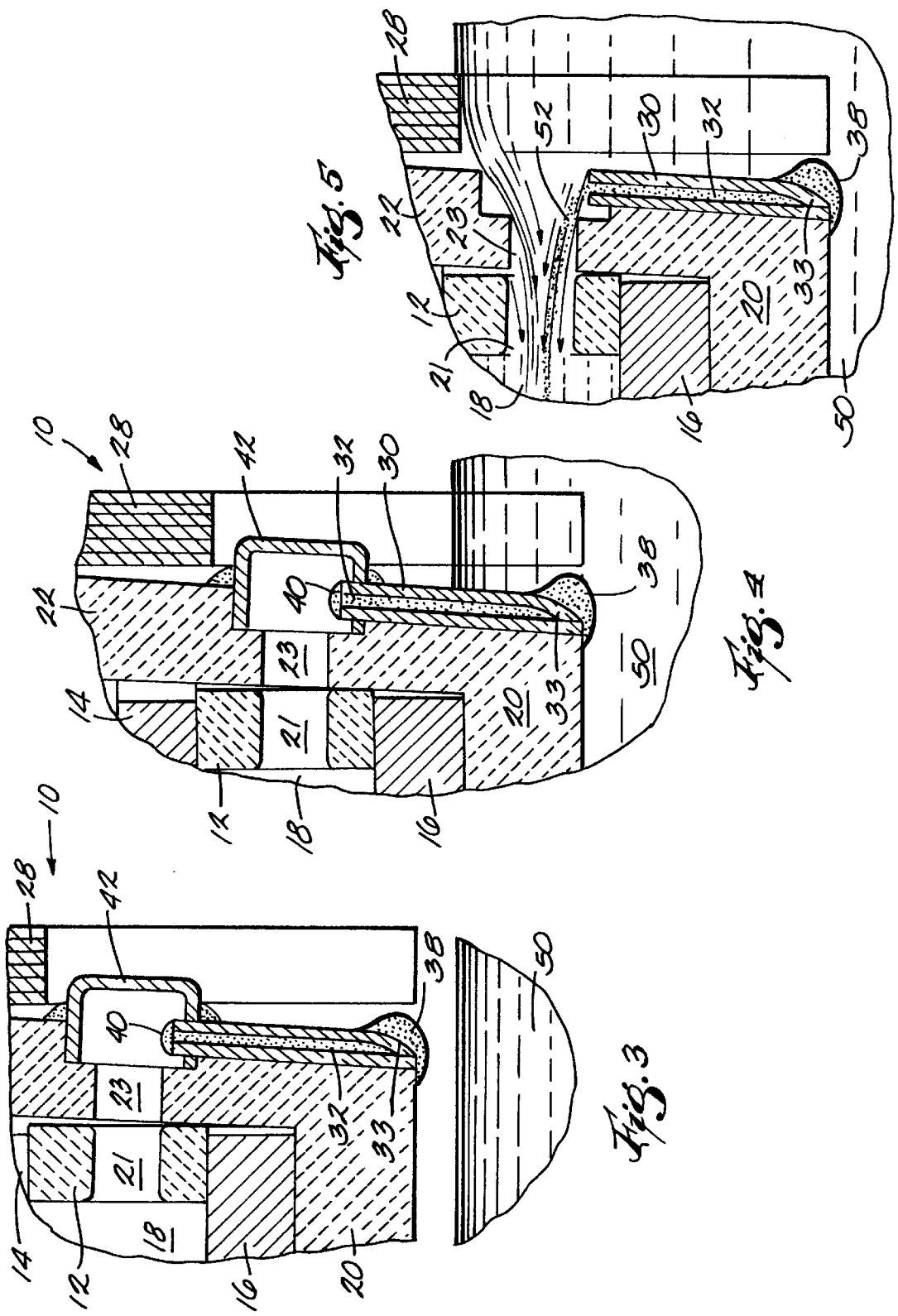

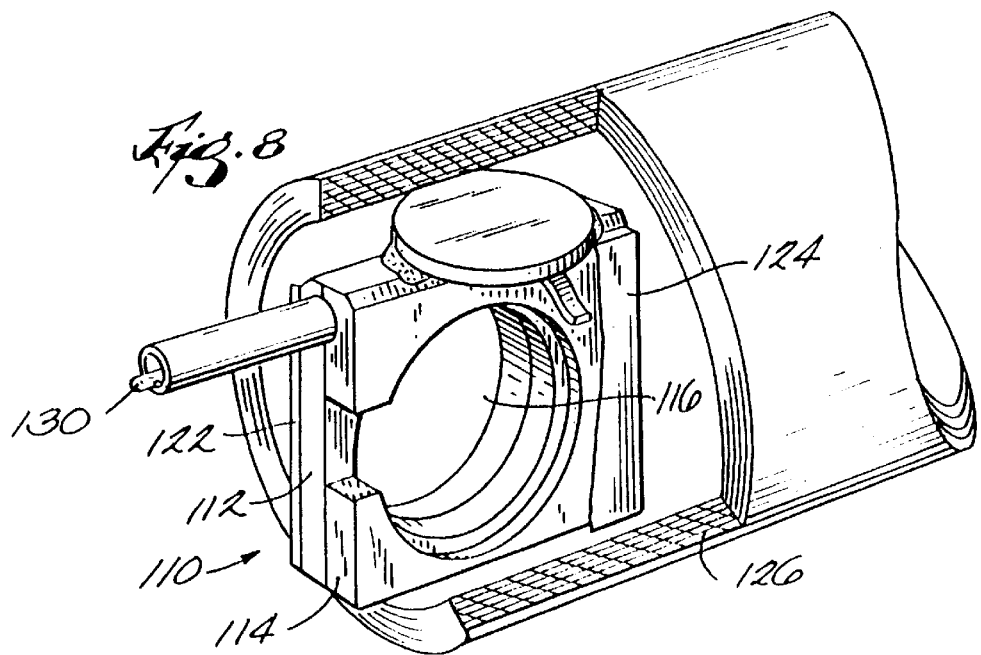
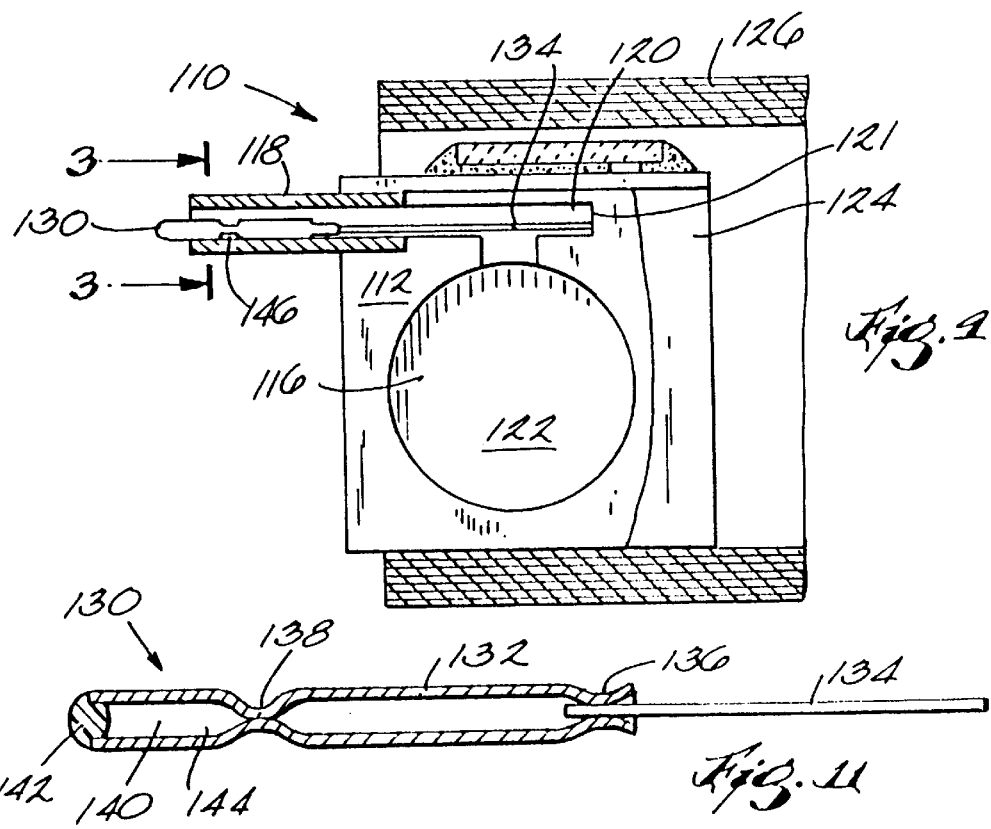
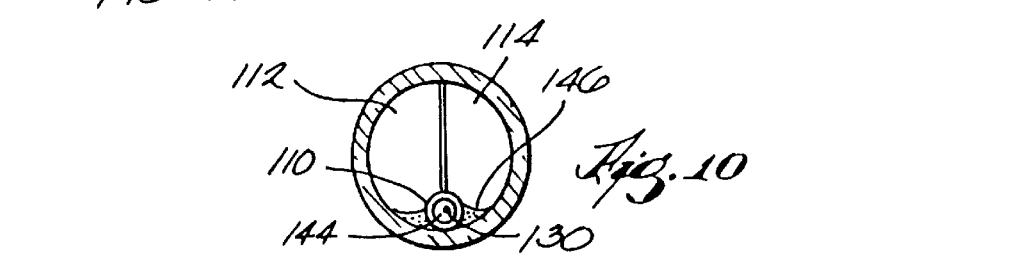

DEVICE FOR DISPENSING ADDITIVE IN MOLTEN METAL SAMPLE MOLD

BACKGROUND OF THE INVENTION

The present invention relates to molten metal samplers. More specifically, the invention relates to devices having cavities for obtaining samples of a molten metal for the purpose of determining the composition or characteristics of the molten metal by spectrographic analysis, and wherein provision is made for adding a material for promoting carbide formation in the molten metal as it cools.

To spectrographically analyze a molten metal to determine its composition, it is common practice to obtain small sample castings or samples for analysis. In order to make an accurate analysis of molten iron, it is desirable to obtain samples of uniform composition, density and structure such as white iron, in which the carbon remains dissolved or interspersed in the metal in the form of a carbide instead of precipitating out in the form of graphite, which results in gray iron or spheroidal/nodular iron. Materials which promote carbide formation and deter graphite formation, such as tellurium, bismuth or antimony have been heretofore coated on mold surfaces fixed in the filling area, or have been placed in the mold in the form of an insert, for example, as described in Falk U.S. Pat. No. 5,524,497 issued Jun. 11, 1996 or U.S. Pat. No. 4,570,496 issued Feb. 18, 1986. U.S. Pat. No. 4,059,996 shows a technique using a "blob" of such material in a cup type mold cavity. Another device for providing an additive such as tellurium to a mold for obtaining samples for spectrographic analysis is described in U.S. Pat. No. 5,057,149 wherein the additive is placed between two flat metal layers.

A need has, however, continued to exist for additional improved techniques for consistently obtaining uniform, homogeneous dense, fine grained metallurgical white iron samples, even if the metal contains high carbon contents or has a high carbon equivalent. Carbon equivalent is defined in U.S. Pat. No. 3,546,921, issued Dec. 15, 1970.

SUMMARY OF THE INVENTION

An important aspect of the present invention is to provide an economical, low cost device for adding tellurium or a similar material by positioning it accurately and reliably at a desired location in or adjacent to an inlet or fill tube which leads to a cavity for obtaining samples of a molten metal for analysis in which carbide formation within the metal is promoted. In one form, the invention permits such positioning partially in and partially outside of the fill tube in the flow path of the molten metal entering the mold.

A further aspect is to provide for such a device wherein an insert is used which provides for the addition, distributed evenly, into the molten metal as it flows into the mold cavity. An accurately measured quantity of tellurium is thus introduced into the sample as it flows into the sampling cavity of a sample mold, thereby assuring consistently accurate analyses, ie., an accurately measured amount of tellurium is added to a measured volume of molten iron. Another advantage provided by the invention is the use of a fusible containers, which temporarily confine the path of distribution of an additive upon immersion of the sampling device into molten metal. A limited portion of the fusible container is more rapidly fusible than the remainder thereof this upon immersion, causing dispensing of the additive in a predictable stream toward or into a fill passage of a metal sampler. Such introduction of the additive over a brief but controlled period of time provides for dispersion and uniform mixing of the additive into the metal sample. A controlled amount and distribution pattern of carbide formation promoting material is thus provided in a sampling cavity. In a preferred embodiment the container body is formed of a fusible metal which is sealed at one end, only, by a more readily fusible or combustible material such as an organic cement.

A still further aspect of the invention relates to improvement of safety to workers by sealing the tellurium additive or similar hazardous material, away from undesirable contact. A further embodiment of the invention involves the ability to easily position the insert in or near a fill tube, the insert being affixed to the mold. The fill opening of a sampling mold then acts as an area in which the carbide formation promoting material is mixed with the metal being sampled as it enters the mold cavity.

A still further advantage is the ability to provide a dimensionally accurate capsule which contains a selected quantity of additive material.

Briefly, the present invention provides a device for sampling molten metals which includes a sample cavity for receiving a measured sample of a molten metal and an insert which contains a material, in finely divided solid form, for promoting carbide formation in the molten metal as it cools, the insert being in the form of an enclosed tube formed of thin-walled material. The insert may be a closed metal container with one end sealed by a relatively low temperature melting or disintegrating material such as an organic polymer. In an alternative embodiment of the invention, any heat consumable material such as an organic polymer may be used as a selected portion of container. The material of the container should be of a consistent mass and be of a type of material which does not interfere with the spectrographic analysis of the sample.

The insert maybe positioned in alignment with a fill inlet passage and is adapted to dispense an additive into molten metal as it flows into the inlet passage. In one embodiment, the capsule is accurately located by means being affixed to or embedded in a surface of the mold adjacent to the fill passage. In an alternate embodiment, a positioning wire is used to accurately locate the capsule prior to being cemented in place. The flowing molten metal will thus be able to melt the selected portion of the insert over a brief period of time to facilitate rapid and thorough introduction of the additive into the metal sample to thereby evenly inoculate the metal with the additive. The main body of the container is subsequently melted.

In accordance with a further preferred aspect of the invention, the insert is in the form of a hollow metal tube which is preferably crimped or otherwise molded closed at one end and open at an opposite end which is closed to contain the additive material by a relatively more easily disintegratable closing material. The containing tube thus has an open end which is closed by means of an adhesive or potting compound such as epoxy cement or by a cap of ablative organic polymer or cellulosic material such as paper adhered over the open end.

Any known form of sampling mold for molten metals may be used such as a mold body formed by first and second mold halves. Each of the mold halves has peripheral edges and the halves define a sample cavity having a fill inlet passage when the mold halves are assembled together. In one embodiment, the mold may be supported on the end of a cardboard tube to assist in the immersion of the mold into molten metal. Details of such devices as further described in my U.S. Pat. Nos. 4,069,717 and 4,140,019, which are incorporated by reference. Other known forms of molds may also be used in conjunction with the invention.

In accordance with the preferred embodiment, the carbide formation promoting material is powdered or granular tellurium. Other such materials, for example, bismuth, cesium, antimony, boron or mixtures thereof can, however, be substituted.

BRIEF DESCRIPTION OF DRAWINGS

The invention will be described in further detail in the following detailed description, claims and accompanying drawings wherein:

FIG. 1 is a perspective view of a mold of usable in connection with the invention with parts disassembled for clarity;

FIG. 2 is a central cross-sectional view of a mold according to FIG. 1 and further fragmentarily showing a supporting lance;

FIGS. 3, 4 and 5 are fragmentary sectional views of the mold shown in FIG. 2 illustrating the sequence occurring upon immersion thereof into a molten metal bath;

FIG. 8 is a fragmentary perspective view of a mold and mold insert of this invention;

FIG. 9 is a fragmentary central sectional view of the mold of FIG. 8;

FIG. 10 is a cross sectional view taken along Line 10—10 of FIG. 9; and

FIG. 11 is a central sectional view of a mold insert of FIG. 10.

DETAILED DESCRIPTION

Figure 6:
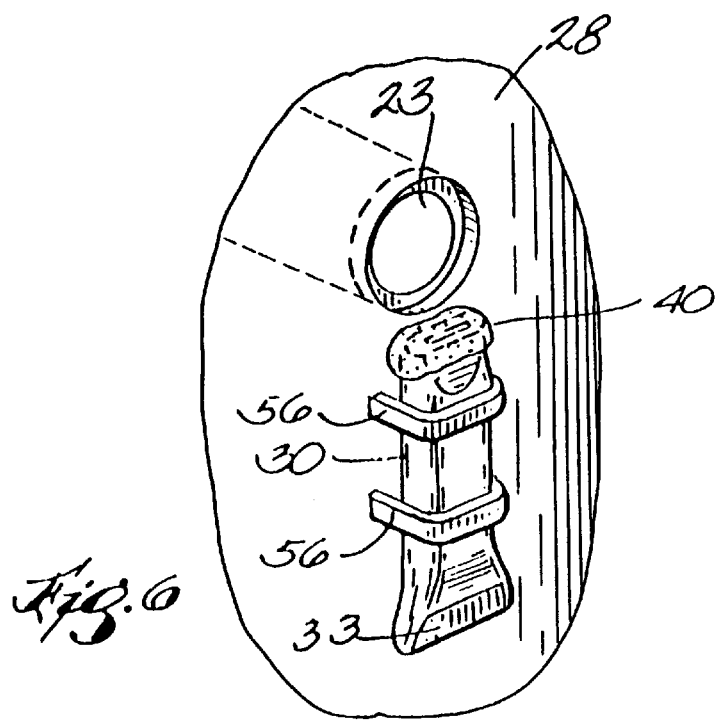
FIG. 6 is a fragmentary perspective view of a mold incorporating a modified embodiment of the invention.

Referring first to FIGS. 1–5 there is seen a preferred embodiment of the invention in conjunction with a mold assembly 10. Mold assembly 10 is a known type of immersion sampling mold used in the metal processing industry. A ring 12 of ceramic material closed on opposite ends by metallic chill plates 14 and 16 forms a mold cavity 18.

Generally cup-shaped members 20 and 22 enclose the mold cavity and the members 12, 14, and 16 which form the cavity. Member 22 is formed with a taper which wedges within the central opening of lower member 20. Hollow upper cavity 23 of member 22 forms a socket for receiving a supporting lance or pole 24 which, in accordance with industry practice may be a metal or cardboard tube. Also, in accordance with customary practice, a cardboard outer sleeve 28 encases the various mold components, as best seen in FIG. 2. Ring 12 is provided with an inlet opening 21 provided to allow the inflow into cavity 18 of molten metal when the mold assembly 10 is immersed in a molten metal bath.

A metal capsule 30 is affixed to the mold. In the embodiment of FIGS. 1–5 capsule 30 is embedded and cemented into a slot formed in the lower edge of cup shaped member 20. Finely divided tellurium or similar additive material 32 is encased in capsule 30. The bottom 36 of capsule 30 is preferably crimped to securely close the same. Refractory cement 38 can be used to cement capsule 30 to cup shaped member 20, the capsule 30 being located so its upper end is approximately aligned with the lower edge of opening 21. A similar opening 23 is formed in the cup-shaped member 20 and aligned with opening 21 to form a fill passage for the sampling mold. The upper end of capsule 30 is closed by means of a readily fusible or combustible material 40, which is preferably an epoxy cement. A temporary cap 42 formed of for example a combustible material such as paper board can be used to close the mold inlet passage 21, 23.

Use of the assembly 10 is illustrated in FIGS. 3–5. As the assembly is immersed in a molten metal bath 50, the capsule 30 remains intact, retaining the additive material contained therein until the lower end of the mold has been immersed as seen in FIG. 5. The crimped end 33 will retain and prevent escape of the additive 32 through bottom end 36 until actual melting of the body of capsule 30 occurs. However, the epoxy cement or similar destructible sealing material 40 enables opening of the upper end of capsule 30 immediately upon immersion into bath 50. Opening of the upper end of the capsule, as illustrated in FIG. 5, combined with the heat provided by the molten metal bath 50 results in expulsion of a stream 52 of particulate additive material which enters the inflowing stream of molten metal 50. This insures dispersion and thorough mixing of the additive 52 into the molten metal 50 which enters the mold cavity 18.

Figure 7:
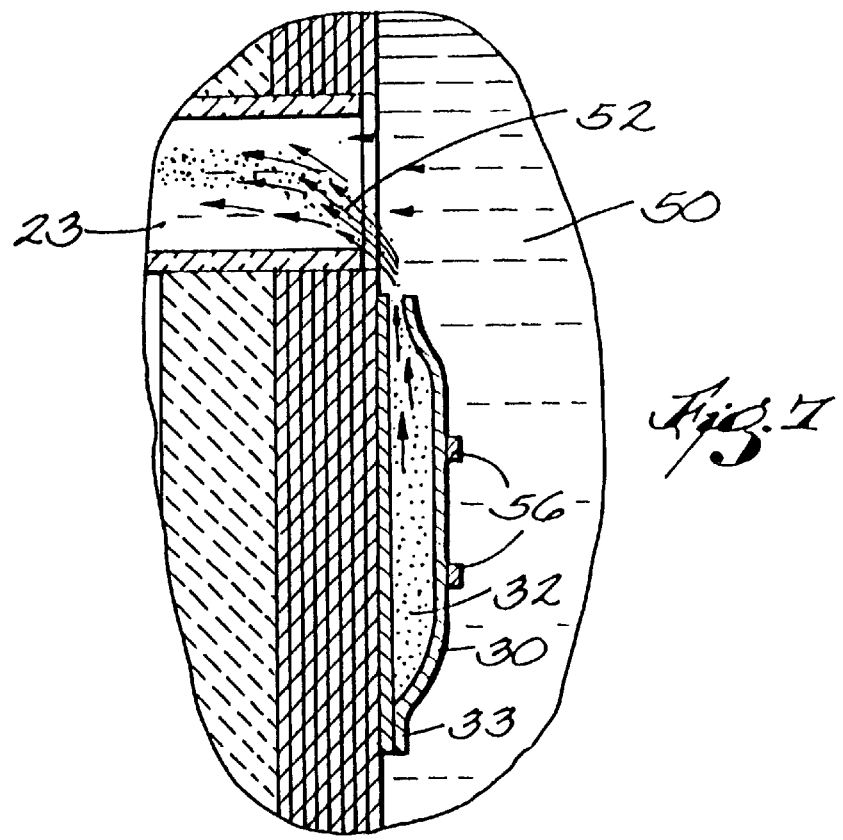
FIG. 7 is a central cross-sectional view showing the immersion of the modified embodiment of FIG. 6 into a molten metal bath.

A somewhat modified embodiment of the invention is shown in FIGS. 6 and 7. Here the capsule 30 is attached to the exterior of the cardboard encasing member 28 by means of U-shaped staples 56 which anchor the capsule 30 in place immediately beneath the mold inlet opening 23 as seen in FIG. 6. As in the case of the earlier embodiment the lower portion 33 of capsule 30 is crimped to seal the same while the upper end 40 is closed by means of an organic adhesive material such as an epoxy resin.

As seen in FIG. 7, once again, when the mold assembly is immersed in molten metal 50 the upper end of the capsule 30 is opened by combustion of the organic adhesive 40, causing stream 52 of finely divided additive material to enter the inlet opening 23 dispersed in the flowing stream of molten metal 50.

An assembled mold assembly pursuant to a further embodiment of the invention 110 is seen in FIGS. 8 and 9. Mold 110 includes mold halves 112 and 114 preferably formed from a ceramic material and mold-closing chill plates 122 and 124 of heat conductive metal, such as steel, which provide for rapid conduction of heat from the molten metal sample. A sample cavity 116 is provided by aligned openings in mold halves 112 and 114. Any conventional clamping or attaching system can be used for closing and holding the halves 112 and 114 of the mold together. Inlet passage 120 is provided for introduction of molten metal into cavity 116. A fill tube 118 is provided for flow into the mold of molten metal to be sampled during immersion of the mold into molten metal and serves as a housing for an insert 130. Fill tube 118 may be secured in place using refractory cement.

Insert 130 contains a material for promoting carbide formation in the molten metal as it cools. A cardboard tube 126 is provided for handling the mold when it is immersed in a molten metal bath, as is known in the art. Preferably the insert 130 is in the form of a tube forming an enclosed section 140 containing the material, such as tellurium 144, in finely divided solid form.

The insert may be adhered within fill inlet passage 124 by means of an adhesive such as a refractory cement. The end of tube 140 may also be closed by means of a paper cap or by epoxy resin 142 to retain the additive 144 in place. The use of an adhesive 146 is not required in all cases, and, thus, while desirable, is optional. Flow of molten metal through tube into opening 124 during immersion of the mold into molten metal causes continuous, time delayed melting of the walls of insert 130 and release of the contents into the molten metal sample as it flows into the mold cavity 116. The metal that flows through tube 18 into cavity 116 becomes mixed with a measured amount of the tellurium sufficient to inhibit graphite formation during solidification and thus to promote the formation of the desired white iron. After cooling of the metal, the mold halves 112, 114 are separated to yield a sample disc of metal for spectrographic analytical testing.

FIG. 11 shows insert 130 in detail. In a preferred embodiment body 132 of insert 130 is formed of a metal such as copper, aluminum or steel, depending on the type of metal to be sampled. Positioning wire 134 is fixed in place by forming a crimp 136 in the tube body 132. A second crimp 38 forms the end of cavity 140 for containment of additive 144. While a fusible metal such as copper is a preferred substance for forming the insert 130, it will be understood that other materials can be substituted. [For example, a polymeric resin can be used, in which case the tube body 132 will vaporize upon contact with the molten metal. In this case it may be preferable to form a bend or an enlargement at the embedded end of wire 134 to ensure that it is positively fixed in the end of the tube body 132.

A measuring device such as a thermocouple or other known device may be used in conjunction with mold 10 for measurement of characteristics such as temperature, dissolved oxygen, carbon or silicon content of the metal sample.

Immersion of mold 110 in a molten metal bath to a depth at which opening fill tube 118 is totally submerged causes rapid, but time delayed, melting or combustion of the outer skin 132 of insert 130 and allows the finely divided solid carbide-forming material within the insert to flow with the molten metal into chamber 149 and to become uniformly mixed with the molten metal to promote carbide formation therein.

In the illustrated embodiment the end of positioning wire 134 abuts against surface 121 in the molten metal fill passageway of the mold 110. If used with molds of other configurations, however, the wire can be dimensioned so that it will contact other interior mold surfaces, dictated by the particular mold configuration. Wire 34 may be any wire, for example, round wire of suitable stiffness. However, other configurations such as rectangular, will serve equally well.

It will be apparent to those skilled in the art that numerous modifications of the aforedescribed preferred embodiment can be made. For example, mold chill plate inserts 122, 124 can be formed from various metals, for example, copper, or steel. With the addition of the carbide formation promoting material it is possible to utilize somewhat less heat conductive material for mold inserts 115 than would otherwise be necessary. Previous methods of adding carbide formation promoting materials to mold often required contaminating binders or coating compositions which retard the release of the carbide former. In contrast, the present invention permits use of a measured quantity of the materials in pure powder form which disperse more rapidly into the molten metal.

When walls 32 are formed of a metal such as copper, the amount of such metal, as an impurity in the sample is accounted for in analysis of the sample by those skilled in the art. It will also be appreciated by those skilled in the art that in addition to tellurium, various other carbide formation promoting materials can be substituted, for example, coating containing bismuth, antimony, boron, cesium or other similar materials known in the art or mixtures thereof.

In addition to the foregoing, various other modifications falling within the scope and spirit of the invention will be apparent to those skilled in the art.

I claim:

1. A sampling device for sampling molten metals comprising:

a mold having sampling cavity for receiving a measured sample of a molten metal and having a fill inlet passage interconnected therewith, an insert containing a composition for promoting carbide formation in the molten metal as it cools affixed to said sampling device, said insert being in the form of a thin-walled tube formed of a first material and having an enclosed portion containing said composition in finely divided solid form, said insert having a closed first end and an opposite second end closed by means of a heat destructible second material, said first material being more heat resistant than said second material whereby said composition is discharged through said second end upon immersion of said device into a molten metal bath, said second end being adjacent to said fill passage.

2. A device according to claim 1 wherein tube is positioned at least partially within said fill inlet passage of said mold.

3. A device according to claim 1 wherein said carbide formation promoting material is selected from the group consisting of tellurium, bismuth, cesium, antimony, boron or mixtures thereof.

4. A device according to claim 1 wherein said first end of said tube is crimped to form said first closed end.

5. A device according to claim 1 wherein the body of said tube is formed of copper, steel or aluminum .

6. A device according to claim 1 wherein said second end is sealed by means of a plastic adhesive material.

7. A device according to claim 1 wherein said tube is mounted in a recess in the body of said mold with said second end positioned in approximate alignment with a side of said fill passage.

8. A mold according to claim 1 wherein said thin walled tube is secured to the interior of said fill passage by means of a refractory cement.

9. A mold according to claim 8 wherein a wire is affixed to said tube, said wire having a free end adapted to engage a surface of said mold to thereby locate said tube in a selected position relative to a fill passage of said mold.

10. A mold according to claim 1 wherein said tube is attached to an outer surface of said sampling device by means of a mechanical fastener.

* * * * *